United States Patent [19]
Nakamura et al.

[11] Patent Number: 4,824,842
[45] Date of Patent: Apr. 25, 1989

[54] CINNAMOYL PIPERIDINES AND THIOMORPHOLINE AND CEREBRAL PROTECTION COMPOSITIONS

[75] Inventors: Joji Nakamura; Kazuhiro Kubo; Shunji Ichikawa; Hajime Takahashi; Keisuke Isozumi; Toyofumi Yamada, all of Shizuoka, Japan

[73] Assignee: Kyowa Hakko Kogyo Kabushiki Kaisha, Japan

[21] Appl. No.: 829,382

[22] Filed: Feb. 13, 1986

[30] Foreign Application Priority Data

Feb. 14, 1985 [JP] Japan ................................. 60-27450

[51] Int. Cl.[4] ................... A61K 31/54; A61K 31/445; C07D 211/22; C07D 265/30
[52] U.S. Cl. ............................. 514/227.5; 514/237.5; 514/330; 544/58.2; 544/58.4; 544/176; 546/216; 546/226
[58] Field of Search ............................ 544/58.2, 58.4; 546/216, 226; 514/222, 234, 238, 330, 227.5, 237.5

[56] References Cited

U.S. PATENT DOCUMENTS 3,590,041 6/1971 Kleemann et al. ............. 546/226 X

OTHER PUBLICATIONS

Turbanti et al., Chemical Abstracts, vol. 69 (1968) 36048k.
Pagani et al., Chemical Abstracts, vol. 79 (1973) 28246q.
Zhang et al., Chemical Abstracts, vol. 93 (1980), 142,676w.
Wang et al., Chemical Abstracts, vol. 97 (1982), 49309z.
Li et al., Chemical Abstracts, vol. 103 (1989), 141582y.
Li et al., Chemical Abstracts, vol. 105, (1986), 218303j.

Primary Examiner—Richard L. Raymond
Attorney, Agent, or Firm—Wolder, Gross & Yavner

[57] ABSTRACT

Compounds of the general formula

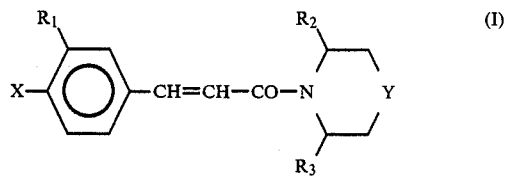

wherein:
  X is halogen or trifluoromethyl;
  $R_1$ is hydrogen, halogen or trifluoromethyl;
  $R_2$ is hydrogen, methyl or hydroxymethyl;
  $R_3$ is hydrogen or lower alkyl; and
  Y is methylene, methylene substituted with a lower alkyl or hydroxyl group, sulfinyl, sulfonyl, oxygen or sulfur, exhibit a cerebral protective effect and are applicable to the treatment of cerebral ischaemia and cerebral hypoxia.

The compounds may be made by acylating a suitable piperidine or morpholine with the appropriate cinnamoyl chloride, and if necessary oxidizing the reaction product.

7 Claims, No Drawings

CINNAMOYL PIPERIDINES AND THIOMORPHOLINE AND CEREBRAL PROTECTION COMPOSITIONS

The present invention relates to an agent for cerebral protection. The term "agent for cerebral protection" denotes an agent for treating acute cerebral ischaemia or cerebral hypoxia, which agent mitigates brain damage due to low oxygen supply, or delays the onset of such damage. Such acute cerebral ischaemia or cerebral hypoxia is caused by cerebral circulation disturbance such as cerebral haemorrhage, cerebral thrombosis, cerebral embolism, subarachnoidal haemorrhage, transient ischaemic attack, hypertensive encephalopathy; cerebral oedema; and external wound to the head, etc.

Various internal treatments have hitherto been proposed for cerebral ischaemia (complete ischaemia), but none of them is yet recognized as of proven reliability.

For instance, it has been known that barbiturates such as thiopental, pentobarbital, mephobarbital, etc, have a cerebral protective activity (Anesthesiology 47, 285 (1977), etc.), and such barbiturates have been used clinically. However, barbiturate therapy (so-called "barbiturate coma therapy") causes a decline of consciousness, suppression of respiration or circulation and disturbances in liver or kidney function, as a result of the powerful anesthetic effect of the high dosages used. The treatment thus needs respiratory and cardiovascular monitoring and involves a distinct hazard.

Further, it has been reported that nizofenone, (1-[2-(2-chlorobenzoyl)-4-nitrophenyl]-2-(diethylaminomethyl)imidazole fumarate) has a cerebral protective effect against cerebral ischaemia or cerebral hypoxia, similar to that of barbiturates, and does not exhibit an anesthetic or respiration-suppressing action different from that of barbiturates [Nihon Rinsho (Japanese Clinic) 43 (2), 185 (1985)].

There has been a need for such medicaments as nizofenone having cerebral protective activity without the accompanying sedation or narcosis and respiratory depression. We have now discovered that a group of compounds has a valuable cerebral protective effect without accompanying such undesirable side effect. Further, the present compounds, in general, are superior to nizofenone in duration of cerebral protective effect and low toxicity.

In one aspect, our invention provides compounds of the general formula

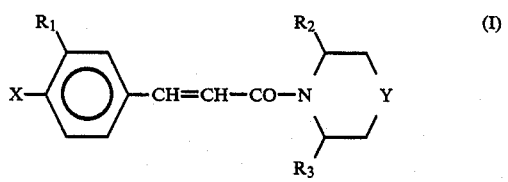

for use in preparing pharmaceutical compositions for the treatment of cerebral ischaemia or cerebral hypoxia, wherein;

X is halogen or trifluoromethyl
$R_1$ is hydrogen, halogen or trifluoromethyl;
$R_2$ is hydrogen, methyl or hydroxymethyl
$R_3$ is hydrogen or lower alkyl; and
Y is methylene, methylene substituted with a lower alkyl or hydroxyl group, sulfinyl, sulfonyl, oxygen or sulfur.

In the definition of $R_3$ of the formula (I), the lower alkyl group includes straight or branched alkyl groups having 1–4 carbon atoms such as methyl or ethyl.

In the definition of Y, the lower alkyl group as a substituent of the methylene group is defined similarly as above. In the definition of X or $R_1$, halogen includes fluorine, chlorine, bromine and iodine.

Compounds (I) exhibit an extremely high and long-lasting cerebral protective activity and a low toxicity. Thus Compounds (I) are expected to be useful as agents for the treatment and rehabilitation of patients having cerebral ischaemia or cerebral hypoxia.

In contrast to barbiturates, Compounds of formula (I) do not result in sedation or narcosis. The duration of action of Compounds (I) is, in general, longer than for nizofenone. Also the acute toxicity of the Compounds (I) is, in general, equal to or lower than the acute toxicity of nizofenone (450–675 mg/kg per os).

The Compounds (I) may be used in the form of a pharmaceutical composition optionally combined with at least one of pharmaceutical carriers, diluents or adjuvants.

Compound (I) may be administered parenterally (for example, intramuscularly, intravenously, subcutaneously, or by rectal administration) or orally, and may be formulated suitably for each method of administration.

Suitable forms for injection are exemplified by aqueous and non-aqueous solutions, suspensions, emulsions and the like. Non-aqueous solvents or vehicles are exemplified by propylene glycol, polyethylene glycol, vegetable oils such as sesame oil, and various esters usable for injection such as ethyl oleate. The above-mentioned pharmaceutical composition may also contain, for example, preservatives, wetting agents, emulsifiers, dispersing agents and other adjuvants. The composition may be sterilized by filtration using a bacterial filter, addition of germicides, irradiation, heating and the like. It is also possible to prepare a sterilized solid composition which may be dissolved in sterilized water before use.

Compositions for oral administration may be formulated into a form suitable for adsorption in the gastrointestinal tract. Tablets, capsules, granules and powders may contain various adjuvants conventionally used in the art such as binders (e.g. syrups, gum arabic, gelatin, sorbitol, tragacanth, polyvinylpyrrolidone, hydroxypropylcellulose); excipients (e.g. lactose, sugar, corn starch, calcium phosphate, sorbitol, glycine); lubricants (e.g. magnesium stearate, talc, polyethylene glycol, silica); disintegrators (e.g. potato starch, carboxymethylcellulose calcium); wetting agents (e.g. sodium lauryl sulfate) and the like. It is also possible to coat the tablets in a conventional manner.

Liquid compositions for oral administration may be formulated into suspensions in water or in oil, solutions, emulsion, syrups and the like. Dry products such as dry syrups may also be used. Such liquid composition and dry products may contain conventional additives such as dispersants (e.g. sorbitol syrup, methylcellulose, glucose sugar syrup, gelatin, hydroxyethylcellulose, carboxymethylcellulose, aluminium stearate gel), emulsifiers (e.g. lecithin, sorbitan monooleate) non-aqueous vehicles (e.g. almond oil, coconut oil and other edible oil, propylene glycol, ethyl alcohol), preservatives (e.g. methyl or propyl p-hydroxybenzoate, sorbic acid).

The compositions for rectal administration may take the form of suppositories and may contain, in addition to the active ingredient, various excipients such as cocoa butter or wax for suppositories.

The amount of Compounds (I) contained in the compositions of the present invention may be varied but is usually 1–20% w/w. The dose of the active ingredient in the composition may be varied depending inter alia upon the route of administration. By way of illustration, a suitable dosage for a human adult is e.g. 10–50 mg/60 kg body weight/day in the case of injection, for example intravenous administration; or 20–100 mg/60 kg body weight/day in the case of oral or rectal administration.

Among the Compounds (I), the following are known in the art:

(i) $X=Cl$, $R_1=R_2=R_3=H$, $Y=CH_2$,
(ii) $X=Cl$, $R_1=R_2=R_3=H$, $Y=O$ and
(iii) $X=R_1=Cl$, $R_2=R_3=H$ and $Y=O$ It is known that these compounds have an anti-convulsive, anti-inflammatory or phytotoxic activity, as reported in Chemical Abstract, 97, 49309z, 1982; ibid., 93, 142676u, 1980 and ibid., 79, 28246q, 1973. However, it has not previously been reported and could not have been predicted that these known compounds and analogues thereof have a novel cerebral protective effect.

Thus another aspect of our invention provides the Compounds (I) excluding the above-mentioned known compounds. Among these new compounds, the cerebral protective activities of the following compounds are superior to the cerebral protecting activities of the above-mentioned known compounds:

(a) $X=Cl$ or $CF_3$, $R_1=H$, $R_2=CH_3$, $R_3=H$ or lower alkyl, and $Y=CH_2$;
(b) $X=CF_3$, $R_1=H$, $R_2=CH_3$, $R_3=H$ or lower alkyl, and $Y=O$;
(c) $X=CF_3$, $R_1=H$, $R_2=H$ or $CH_3$, $R_3=H$ or lower alkyl, and $Y=S$, $-SO-$ or $-SO_2-$.

The Compounds of formula (I) where Y is methylene, methylene substituted with a lower alkyl or hydroxyl group, oxygen, or sulfur, may be produced by reacting a compound of formula:

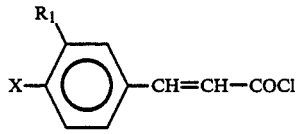

(wherein X and $R_1$ are as hereinbefore defined) with a compound of the formula:

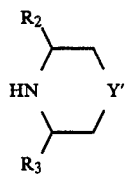

(wherein $R_2$ and $R_3$ are as hereinbefore defined, and $Y'$ is methylene, methylene substituted with a lower alkyl or hydroxyl group, oxygen, or sulfur) in an inert solvent optionally in the presence of an acid-binding agent for binding the hydrochloric acid.

Solvents which may be used for the reaction are exemplified by water, methanol, ethanol, isopropanol and other alcohols; acetone, methyl ethyl ketone and other ketones; benzene, toluene, xylene and other aromatic hydrocarbons; chloroform, carbon tetrachloride, dichloromethane, dichloroethane and other halogenated lower alkanes; acetonitrile, dimethylformamide, dimethylacetamide, dimethylsulfoxide and other aprotic polar solvents, and the like. Although the use of the acid-binding agent is not always, required, it is possible to use triethylamine, pyridine, dimethylaniline and other organic bases; and sodium bicarbonate, sodium carbonate, sodium hydroxide and other inorganic bases to make the reaction proceed smoothly. The reaction may preferably be effected at a temperature of $-10°$ to $100°$ C., more particularly from $-5°$ to $50°$ C. The reaction is usually completed by 0.5–20 hours.

A Compound (I) where Y is sulfinyl may be produced by oxidizing a Compound (I) where Y is sulfur with an oxidizing agent such as sodium periodate in an inert solvent such as water, methanol, ethanol, acetic acid, dioxane at $-10°-100°$ C. for 2–6 hours. A Compound (I) where Y is sulfonyl may be produced by oxidizing a Compound (I) where Y is sulfur with an oxidizing agent such as hydrogen peroxide in an inert solvent. The similar inert solvents, reaction temperature and reaction time as above oxidation can be employed.

The following Examples and experiments illustrate the invention.

EXAMPLE 1

2-Methylpiperidine (4.2 g; 0.042 mol) and triethylamine (4.7 g; 0.047 mol) are dissolved in anhydrous benzene (40 ml). To this solution are added dropwise a solution of 4-trifluoromethylcinnamoyl chloride (10 g; 0.042 mol) in anhydrous benzene (10 ml) at 10°–15° C. over a period of 10 minutes. After the addition, the mixture is stirred at room temperature for 2 hours to precipitate triethylamine hydrochloride which is removed by filtration. The filtrate is concentrated under reduced pressure. The residue is recrystallized from ligroin to obtain 2-methyl-1-(4-trifluoromethylcinnamoyl) piperidine (referred to as Compound 1) (10.2 g, yield 80.5%) as white powder.

Melting point: 88°–89° C.

IR $\nu_{max}^{KBr}$ cm$^{-1}$: 1642 (C=O), 1595 (C=C), 1320 (C—F).

NMR (CDCl$_3$)δ: 1.27(3H, d, J=7 Hz), 1.67(6H, br.s), 2.73–3.33(1H, m), 4.12–4.72(2H, m), 6.90(1H, d, J=16 Hz), 7.57(4H, s), 7.59(1H, d, J=16 Hz).

Elemental analysis (as C$_{16}$H$_{18}$F$_3$NO) (%):

|  | C | H | N |
| --- | --- | --- | --- |
| Calculated: | 64.64 | 6.10 | 4.71 |
| Found: | 64.48 | 5.91 | 4.91 |

EXAMPLE 2

3-Methylmorpholine (1.5 g; 0.015 mol) and sodium bicarbonate (1.7 g; 0.02 mol) are suspended and dissolved in acetone (20 ml). The solution is cooled to 0°–5° C. Then, a solution of 4-trifluoromethylcinnamoyl chloride (2.8 g; 0.012 mol) in acetone (5 ml) is added dropwise to the solution over a period of 2 minutes. After the addition, the mixture is stirred at room temperature for one hour and poured into ice water (100 ml). The separated oily material is extracted with toluene. The toluene layer is washed successively with water, 5% aqueous hydrochloric acid and water, followed by drying with anhydrous sodium sulfate. By removing toluene under reduced pressure 3-methyl-4-

(4-trifluoromethylcinnamoyl)morpholine (referred to as Compound 2) (3.1 g; yield 86.3%) is obtained as colourless prisms.

Melting point: 88°–92° C.

IR $\nu_{max}^{KBr}$ cm$^{-1}$: 1645 (C=O), 1600 (C=C), 1320 (C—F).

NMR (CDCl$_3$)δ: 1.35(3H, d, J=7 Hz), 3.10–4.55(7H, m), 6.69(1H, d, J=15 Hz), 7.37(4H, s), 7.42(1H, d, J=15 Hz).

Elemental analysis (as C$_{15}$H$_{16}$F$_3$NO$_2$) (%):

|  | C | H | N |
|---|---|---|---|
| Calculated: | 60.20 | 5.39 | 4.68 |
| Found: | 59.90 | 5.45 | 4.78 |

In a similar manner to that described above, the following compounds are obtained:

2-Methyl-1-(4-chlorocinnamoyl)piperidine (Compound 3):

Melting point: 113° C., white powder (ligroin).

Yield: 79.3%.

Ir $\nu_{max}^{KBr}$ cm$^{-1}$: 1650 (C=O), 1600 (C=C).

NMR (CDCl$_3$)δ: 1.23(3H, d, J=7 Hz), 1.65(6H, br.s), 2.80–3.19(1H, m), 4.09–4.70(2H, m), 6.80(1H, d, J=16 Hz), 7.23–7.50(4H, m), 7.53(1H, d, J=16 Hz).

Elemental analysis (as C$_{15}$H$_{18}$ClNO) (%):

|  | C | H | N |
|---|---|---|---|
| Calculated: | 68.30 | 6.88 | 5.31 |
| Found: | 67.70 | 6.58 | 5.29 |

2-Methyl-1-(4-fluorocinnamoyl)piperidine (Compound 4):

Melting point: 113.5°–115.5° C., white needles (benzene-hexane).

Yield: 77.8%.

IR $\nu_{max}^{KBr}$ cm$^{-1}$: 1650 (C=O), 1620 (C=C).

NMR (CDCl$_3$)δ: 1.22(3H, d, J=7 Hz), 1.63(6H, br.s), 2.77–3.20(1H, m), 4.03–4.63(2H, m), 6.59–7.63 (6H, m).

Elemental analysis (as C$_{15}$H$_{18}$FNO) (%):

|  | C | H | N |
|---|---|---|---|
| Calculated: | 72.85 | 7.34 | 5.66 |
| Found: | 72.22 | 7.07 | 5.81 |

2,6-Dimethyl-1-(4-trifluoromethylcinnamoyl) piperidine (Compound 5):

Melting point: 89°–91° C., light brownish flake crystals (benzene-hexane).

Yield: 71.1%.

IR $\nu_{max}^{KBr}$ cm$^{-1}$: 1643 (C=O), 1595 (C=C), 1320 (C—F).

NMR (CDCl$_3$)δ: 1.30(6H, d, J=7 Hz), 1.69(6H, br.s), 4.37–4.90(2H, m), 6.92(1H, d, J=16 Hz), 7.57(4H, s), 7.63(1H, d, J=16 Hz).

Elemental analysis (as C$_{17}$H$_{20}$F$_3$NO) (%):

|  | C | H | N |
|---|---|---|---|
| Calculated: | 65.58 | 6.48 | 4.50 |
| Found: | 64.93 | 6.25 | 4.95 |

4-(4-Fluorocinnamoyl)morpholine (Compound 6):

Melting point: 136°–137° C., light yellowish needles (benzene).

Yield: 33%.

IR $\nu_{max}^{KBr}$ cm$^{-1}$: 1650 (C=O), 1610 (C=C).

NMR (CDCl$_3$)δ: 3.76(8H, s), 6.80(1H, d, J=16 Hz), 7.45(4H, s), 7.57(1H, d, J=16 Hz).

Elemental analysis (as C$_{13}$H$_{14}$FNO$_2$) (%):

|  | C | H | N |
|---|---|---|---|
| Calculated: | 66.37 | 6.00 | 5.95 |
| Found: | 65.99 | 5.84 | 5.96 |

4-(4-Trifluoromethylcinnamoyl)morpholine (Compound 7):

Melting point: 142°–143.5° C., colourless needles (benzene-ligroin).

Yield: 89.7%.

IR $\nu_{max}^{KBr}$ cm$^{-1}$: 1655 (C=O), 1610 (C=C), 1325 (C—F).

NMR (CDCl$_3$)δ: 3.62(8H, s), 6.67–7.69(6H, m).

Elemental analysis (as C$_{14}$H$_{14}$F$_3$NO$_2$) (%):

|  | C | H | N |
|---|---|---|---|
| Calculated: | 58.95 | 4.95 | 4.91 |
| Found: | 58.72 | 4.97 | 4.87 |

4-Methyl-1-(4-trifluoromethylcinnamoyl)piperidine (Compound 8):

Melting point: 90°–91° C., white needles (ligroin).

Yield: 76%.

IR $\nu_{max}^{KBr}$ cm$^{-1}$: 1650 (C=O), 1600 (C=C), 1325 (C—F).

NMR (CDCl$_3$)δ: 0.99(3H, d), 1.20–4.77(9H, m), 6.89(1H, d, J=16 Hz), 7.50(1H, d, J=16 Hz), 7.58(4H, s).

Elemental analysis (as C$_{16}$H$_{18}$F$_3$NO) (%):

|  | C | H | N |
|---|---|---|---|
| Calculated: | 64.64 | 6.10 | 4.71 |
| Found: | 64.91 | 6.08 | 4.95 |

2-Hydroxymethyl-1-(4-trifluoromethylcinnamoyl) piperidine (Compound 9):

Melting point: 139°–140° C., white needles (n-hexane-benzene).

Yield: 43%.

IR $\nu_{max}^{KBr}$ cm$^{-1}$: 1650 (C=O), 1590 (C=C).

NMR (CDCl$_3$)δ: 1.3–1.93(6H, br.s), 2.73–3.4(1H, br.s), 3.53–4.83(3H, br.s), 6.93(1H, d, J=15 Hz), 7.43(4H, s), 7.53(1H, d, J=15 Hz).

4-Hydroxy-1-(4-trifluoromethylcinnamoyl)piperidine (Compound 10):

Melting point: 124°–135° C., white needles (n-hexane-benzene).

Yield: 77%.

IR $\nu_{max}^{KBr}$ cm$^{-1}$: 1645 (C=O), 1590 (C=C).

NMR (CDCl$_3$)δ: 1.23–2.27(4H, m), 3.13–3.67(2H, m), 3.7–4.4(3H, br.s), 4.23(1H, d, J=15 Hz), 7.57(4H, s), 7.63(1H, d, J=15 Hz).

4-(4-Trifluoromethylcinnamoyl)thiomorpholine (Compound 11):

Melting point: 136°–137° C., light yellowish brown needles (n-hexane-benzene).

Yield: 85.3%.

IR $\nu_{max}^{KBr}$ cm$^{-1}$: 1655 (C=O), 1615 (C=C).

NMR (CDCl$_3$)δ: 2.53–2.83(4H, m), 3.83–4.13(4H, m), 6.87(1H, d, J=16 Hz), 7.53(4H, s), 7.6(1H, d, J=16 Hz).

EXAMPLE 3

Sodium periodate (1.49 g, 0.007 mol), water (50 ml) and methanol (50 ml) are mixed. To the mixture is added dropwise a solution of 4-(4-trifluoromethyl-cinnamoyl) triomorpholine (Compound 11) (2.0 g, 0.007 mol) in methanol (80 ml) under ice cooling. Then, the mixture is stirred under ice cooling for 5 hours and further overnight at room temperature, and the precipitate is removed by filtration. The filtrate is concentrated under reduced pressure, and the residue is dried and recrystallized from benzene (100 ml) to obtain 4-(4-trifluoromethyl-cinnamoyl) thiomorpholine-1-oxide (Compound 12) (1.4 g, yield 66.6%) as colorless needles.

Melting point: 187°–188° C.

IR $\nu_{max}^{KBr}$ cm$^{-1}$: 1650 (C=O), 1650 (C=C).

NMR (d$^6$–DMSO)δ: 2.7–3.07(4H, m), 3.47–4.27(4H, br.s), 7.48(2H, s), 7.68(2H, d, J=9 Hz), 7.93(2H, d, J=9 Hz).

EXAMPLE 4

4-(4-trifluoromethylcinnamoyl)thiomorpholine (Compound 11) (3.0 g, 0.01 mol), acetic acid (40 ml) and hydrogen peroxide (5 ml) are entered in a reaction flask and stirred with heating at 80° C. for 8 hours. After completion of the reaction, the mixture is poured into water. The precipitate is collected by filtration and recrystallized from ethanol (50 ml) to obtain 4-(4-trifluoromethyl-cinnamoyl) thiomorpholine-1,1-dioxide (Compound 13) (1.5 g, yield 45.3%) as light milk white crystals.

Melting point: 162°–163° C.

IR $\nu_{max}^{KBr}$ cm$^{-1}$: 1650 (C=O), 1615 (C=C), 1325, 1125 (S=O).

NMR (d$^6$–DMSO)δ: 3.07–3.6(4H, br.s), 3.9–4.4(4H, br.s), 7.43–7.63(2H, br.s), 7.7(2H, d, J=9 Hz), 7.93(2H, d, J=9 Hz)

EXAMPLE 5

Tablet

Tablets having the following composition are prepared in conventional manner:

| | |
|---|---|
| Compound 1 | 20 mg |
| Lactose | 60 mg |
| Potato starch | 30 mg |
| Polyvinyl alcohol | 2 mg |
| Magnesium stearate | 1 mg |
| Synthetic colouring | trace |

EXAMPLE 6

Powder

Dosage units in powder form having the following composition are prepared in conventional manner:

| | |
|---|---|
| Compound 2 | 20 mg |
| Lactose | 280 mg |

EXAMPLE 7

Suppository

Suppositories having the following composition are prepared in conventional manner:

| | |
|---|---|
| Compound 3 | 30 mg |
| Macrogol 1500 | 900 mg |
| Macrogol 4000 | 900 mg |
| (Macrogol is polyethylene glycol) | |

EXPERIMENT 1

Test for acute toxicity

Mice (ddY strain; male; body weight 21–23 g) were used as test animals. Each group consisted of 5 mice. The test compound was orally administered to each mouse. During the test period of 7 days after the administration, the number of deaths in each group was counted to calculate the LD$_{50}$. All animals were bred in a breeding room, maintained at a temperature of 23±2° C. and a humidity of 55–60%. These animals were given a solid feed "F-2" (commercial product of Funabashi Nojo) and city water ad libitum. The results are shown in Table 1.

TABLE 1

| No. | 1 | 2 | 3 | 4 | 5 | 6 | 7 | 8 | *14 | *15 | *16 |
|---|---|---|---|---|---|---|---|---|---|---|---|
| LD$_{50}$ | >1012 | 675–1012 | >1012 | >1012 | >1012 | >1012 | 300–450 | >1012 | >1012 | 450–675 | 675–1012 |

No. = compound number;
LD$_{50}$ = LD$_{50}$ (mg/kg)
*14: 1-(4-chlorocinnamoyl)piperidine
15: 4-(3,4-dichlorocinnamoyl)morpholine
16: 4-(4-chlorocinnamoyl)morpholine

EXPERIMENT 2

Effects on survival time of mice subjected to normobaric hypoxia

Mice (ddY strain; male; body weight 20–22 g) were used as test animals. Each group consisted of 10 or more mice. A test compound (50 mg/kg) was orally administered to each mouse. Two hours after the administration, all animals showed no accompanying sedation or narcosis since it was observed that the righting reflex still persisted in all animals.

Then each animal was put into a glass cylinder (capacity: 700 ml) and a mixture of nitrogen (96%) and oxygen (4%) was passed through the cylinder at a velocity of 5 l/min and expelled through a hole in the side wall. The time from the start of the gas mixture supply to the cessation of respiratory motion was measured, and animals which remained alive for 10 or more minutes were evaluated as "protected". Among 50 untreated animals, no animal remained alive. In use, the test compound was suspended in an aqueous solution of carboxymethylcellulose sodium (0.3%). The number of "protected" animals is shown in Table 2.

TABLE 2

| No. | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| A/B | 10/10 | 8/10 | 9/10 | 7/20 | 15/20 | 2/10 | 4/10 | 5/20 | 2/10 | 2/10 | 7/10 | 8/10 | 6/10 | 4/10 | 5/10 | 5/10 |

Notes:
No. Compound number,
A number of animals surviving
B number of animals tested

EXPERIMENT 3

Effects on survival time of mice subjected to hypobaric hypoxia

Mice (ddY strain; male; body weight 20–22 g) were used as test animals. Each group consisted of 10 or more mice. A test compound (30 mg/kg) was orally administered to each mouse. Two hours after the administration, each animal was put into a desiccator (capacity: 9 l), and the inside pressure of the desiccator was reduced to 150 mmHg over a period of 52–55 seconds. The time from the start of the pressure reduction to the cessation of respiratory motion was measured. Survival time of the compound-administered group and that of the control group were compared by t-test. It was judged that the test compound had a cerebral protective activity when a significant extension of survival time was observed with less than a 5% level of significance.

The results are shown in Table 3.

TABLE 3

|  | Compound No. | | | |
|---|---|---|---|---|
|  | 1 | 3 | 4 | Control |
| Survival Time (sec.) | 582.8 ± 12.1** | 172.4 ± 11.3** | 126.3 ± 6.9* | 109.5 ± 2.8 |

Values represent mean values ± S.E.
*$P < 0.05$,
**$P < 0.001$

EXPERIMENT 4

Effects on survival time of mice subjected to anaemic hypoxia (Hypoxia induced by $NaNO_2$ administration to convert haemoglobin to methemoglobin)

Mice (ddY strain; male; body weight 20–22 g) were used as test animals. Each group consisted of 10 or more mice. A test compound (30 mg/kg) was orally administered to each mouse. Two hours after the administration, $NaNO_2$ (225 mg/kg) was subcutaneously administered to each mouse. The time from the $NaNO_2$ administration to death was measured. Survival time of the compound-administered group and that of the control group were compared by t-test. The test compound was judged to have a cerebral protective activity when a significant extension of survival time was observed with less than a 5% level of significance.

The results are shown in Table 4.

TABLE 4

|  | Compound No. | | | |
|---|---|---|---|---|
|  | 1 | 3 | 4 | Control |
| Survival Time (min.) | 64.9 ± 5.5** | 47.7 ± 5.5* | 58.4 ± 5.5** | 35.0 ± 1.6 |

Note:
Cf. Table 3 for explanation of statistical abbreviations.

EXPERIMENT 5

Effect on time of gasping persistence by decapitated heads of mice

Mice (ddY strain; male; body weight 20–22 g) were used as test animals. Each group consisted of 10 or more mice. A test compound (30 mg/kg) was orally administered to each mouse. Two hours after the administration, each animal was decapitated, and the time from the decapitation to the cessation of gasping was measured. Time of gasping persistence of the treated group and that of the control group were compared by t-test. The test compound was judged to have a cerebral protective activity when significant extension of gasping time was observed with less than a 5% level of significance.

The results are shown in Table 5.

TABLE 5

|  | Compound No. | | | |
|---|---|---|---|---|
|  | 1 | 3 | 4 | Control |
| Persistence Time (sec.) | 39.1 ± 1.4** | 30.2 ± 1.1** | 23.5 ± 0.8** | 20.0 ± 0.3 |

Note:
Cf. Table 3 for explanation of statistical abbreviations.

What is claimed is:

1. Compounds of the formula $$X-\text{C}_6\text{H}_4-CH=CH-CO-N\underset{R_3}{\overset{R_2}{\diagup}}Y \quad (I)$$

wherein
X is selected from the group of chloro and trifluromethyl;
$R_2$ is selected from the group of hydrogen and methyl;
$R_3$ is selected from the group of hydrogen and methyl; and
Y is selected from the group of methylene, sulfinyl, sulfonyl and sulphur; provided that:
(a) when Y is methylene at least one of $R_2$ and $R_3$ is methyl; (b) when Y is sulfinyl, sulfonyl or sulphur X is not chloro.

2. The compound of claim 1 which is 2-methyl-1-(4-trifluoromethylcinnamoyl)piperidine.

3. 2-methyl-1-(4-(chlorocinnamoyl)piperidine.

4. 4-(4-trifluoro-methylcinnamoyl)thiomorpholine.

5. 4-(4-trifluoro-methylcinnamoyl)thiomorpholine-1-oxide.

6. 4-(4-trifluoro-methylcinnamoyl)thiomorpholine-1,1-dioxide.

7. A pharmaceutical composition comprising a pharmacologically effective amount of a compound of any of claims 1, 2, 3, 4, 5 or 6 and at least one of pharmaceutically acceptable carriers, excipients or adjuvants.

* * * * *

UNITED STATES PATENT AND TRADEMARK OFFICE
CERTIFICATE OF CORRECTION

PATENT NO. : 4,824,842
DATED : APRIL 25, 1989
INVENTOR(S) : JOJI NAKAMURA; KAZUHIRO KUBO; SHUNJI ICHIKAWA; HAJIME TAKAHASHI; KEISUKE ISOZUMI and TOYOFUMI YAMADA It is certified that error appears in the above-identified patent and that said Letters Patent is hereby corrected as shown below:

On the title page, item [73]

Assignee: Kyowa Hakko Kogyo Kabushiki Kaisha;
Ihara Chemical Kogyo Kabushiki Kaisha,
both of Japan Signed and Sealed this Twenty-second Day of October, 1991

Attest:

HARRY F. MANBECK, JR.

Attesting Officer

Commissioner of Patents and Trademarks